(12) United States Patent
Katzer et al.

(10) Patent No.: US 7,925,606 B1
(45) Date of Patent: Apr. 12, 2011

(54) MONITORING PHYSICAL LOCATIONS USING RULES AND EVENTS PROCESSING

(75) Inventors: Robin Dale Katzer, Olathe, KS (US); Lynn Neir, Overland Park, KS (US); Charles D. Stunson, Overland Park, KS (US)

(73) Assignee: Sprint Communications Company L.P., Overland Park, KS (US)

( * ) Notice: Subject to any disclaimer, the term of this patent is extended or adjusted under 35 U.S.C. 154(b) by 774 days.

(21) Appl. No.: 11/857,021

(22) Filed: Sep. 18, 2007

(51) Int. Cl.
*G06F 15/18* (2006.01)
*G06F 15/00* (2006.01)
*G01S 3/801* (2006.01)

(52) U.S. Cl. ................... 706/47; 705/2; 367/99
(58) Field of Classification Search .......... 706/2, 6, 706/46–48; 705/2; 707/2, 10, 103
See application file for complete search history.

(56) References Cited

U.S. PATENT DOCUMENTS

| | | | |
|---|---|---|---|
| 4,189,719 A | 2/1980 | Massa et al. | |
| 4,229,811 A | 10/1980 | Salem | |
| 4,242,743 A | 12/1980 | Salem | |
| 4,512,000 A | 4/1985 | Masuko | |
| 4,815,046 A | 3/1989 | Dorr | |
| 4,875,198 A | 10/1989 | Ariav | |
| 4,939,701 A | 7/1990 | Brunner et al. | |
| 5,802,494 A * | 9/1998 | Kuno ................... | 705/2 |
| 6,490,574 B1 * | 12/2002 | Bennett et al. ................... | 706/47 |
| 6,560,592 B1 * | 5/2003 | Reid et al. ..................... | 1/1 |
| 7,049,960 B2 | 5/2006 | Waltermann | |
| 7,710,824 B1 | 5/2010 | Katzer et al. | |
| 2005/0225427 A1 | 10/2005 | Bell et al. | |

OTHER PUBLICATIONS

Jih et al, "A Multi-Agent Service Framework for Context-Aware Elder Care", in AAMAS' 2006 Workshop on Service-Oriented Computing and Agent-Based Engineering (SOCABE'2006), May 8-12, 2006, pp. 61-75.*
Notice of Allowance dated Dec. 17, 2009, 5 pages, U.S. Appl. No. 11/857,033, filed Sep. 18, 2007 IDF 4965.
Office Action dated Jul. 10, 2009, 7 pages, U.S. Appl. No. 11/857,033, filed Sep. 18, 2007 IDF 4965.
Katzer, Robin Dale, et al., "Location Monitoring and Sonar Determination of Presence," U.S. Appl. No. 11/857,033, filed Sep. 18, 2007 IDF 4965.

* cited by examiner

*Primary Examiner* — Michael B. Holmes
*Assistant Examiner* — Ola Olude-Afolabi (57) ABSTRACT

A monitoring system is provided. The monitoring system comprises a first storage queue containing rules ready for processing, an event storage containing events, and a plurality of first processor threads configured to execute any one of the rules contained in the first storage queue based on the contents of the event storage. The system also comprises a rules processor configured to receive a plurality of events from a plurality of monitored locations, to add the event to the event storage, to remove a first rule from the first storage queue, to provide the first rule to one of the first processor threads for executing, to receive a first result from the one of the first processor threads, and to send a first notification based on the first result.

20 Claims, 6 Drawing Sheets

MONITORING PHYSICAL LOCATIONS USING RULES AND EVENTS PROCESSING

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Improvements in healthcare, diets, safety, and other considerations are permitting people to live longer. Elderly people often prefer to retain their autonomy and their freedom and continue to live in their own homes as long as possible, rather than moving, for example, to a nursing home. Societies everywhere are becoming increasingly mobile and dispersed. Children who formerly settled close to their birthplace now may settle several hundreds of miles away from their birthplace, far from their parent's residence. Additionally, both men and women often work outside the home. Children may feel nervous about their elderly parent continuing to live in their own homes rather than in a nursing home, being concerned that if a medical crisis strikes their elderly parent it may be a long time before the crisis becomes known.

SUMMARY

In an embodiment, a monitoring system is provided. The monitoring system comprises a first storage queue containing rules ready for processing, an event storage containing events, and a plurality of first processor threads configured to execute any one of the rules contained in the first storage queue based on the contents of the event storage. The system also comprises a rules processor configured to receive a plurality of events from a plurality of monitored locations, to add the event to the event storage, to remove a first rule from the first storage queue, to provide the first rule to one of the first processor threads for executing, to receive a first result from the one of the first processor threads, and to send a first notification based on the first result.

In another embodiment, a method of monitoring locations is provided. The method comprises adding a plurality of static rules to a static rules queue, each static rule associated with one of the locations; adding a plurality of dynamic rules to a dynamic rules queue, each dynamic rule associated with one of the locations; and adding a plurality of events to an event store, at least some of the events associated with the locations. The method also comprises removing a first static rule from the static rules queue for processing, returning the first static rule to the static rules queue for later processing, matching a first event in the event store with the first static rule, the matching based at least in part on the location associated with the first event and with the first static rule, and processing the first static rule based on the first event. The method also comprises removing a first dynamic rule from the dynamic rules queue for processing, returning the first dynamic rule to the dynamic rules queue for later processing; matching a second event in the event store with the first dynamic rule, the matching based at least in part on the location associated with the second event and with the first dynamic rule, and processing the first dynamic rule based on the second event. The static rules are defined with reference to a start time and an end time, and the dynamic rules are defined with reference to an elapsed time since an associated event.

In still another embodiment, a method for providing elder care is disclosed. The method comprises detecting a plurality of motions at an elder care location, determining if the detection of motions occurs during an expected time interval based on a first plurality of rules data, and sending a first notification that expected motions occurred based on the first plurality of rules data.

These and other features will be more clearly understood from the following detailed description taken in conjunction with the accompanying drawings and claims.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

DETAILED DESCRIPTION

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

The disclosure describes a scaleable system that concurrently monitors events at a large number of buildings and/or dwellings and at multiple locations within any one of the buildings and/or dwellings. The monitoring system generates positive messages for expected events at the monitored locations and negative messages for unexpected events at the monitored locations or the lack of events at the monitored locations at expected times. These events, for example, may include motion in a bedroom, motion in a hallway, opening a door of a refrigerator, opening a door of a house, and other events. The system sends the positive and negative messages to, for example, subscribers of the monitoring system who may be children of elderly people living on their own or a small business owner.

Elderly people may experience a health crisis during the night, for example a stroke, which prevents them from rising and moving about their residence in the morning. Additionally, elderly people may fall in their bathroom and be unable to get up. The monitoring system provides a flexible event scenario description capability for describing the rules for sending positive messages and the rules for sending negative messages, enabling customized monitoring rules for a large number of monitoring service subscribers. In other embodiments, however, the events monitoring system monitors other kinds of locations, for example business facilities. The rules include static rules and dynamic rules. Static rules may be launched or triggered at pre-defined times associated with expected actions, for example an expected time for an elderly person to rise from bed between 7 AM and 8 AM. Dynamic rules may be launched or triggered by pre-defined actions instead of times, and subsequent events may be linked to the dynamic trigger based on timing referenced to the initial triggering action.

The architecture of the monitoring system readily supports scaling to a number of service subscribers, for example thousands or millions of subscribers, by storing the rule definition and rule state information of the many active rules on queues and instantiating the processing instructions associated with applying the rules for only a subset of the active rules at any time. Alternatively, this architecture supports monitoring a large number of different rules or rule chains within a single facility or a small number of facilities, for example a manufacturing plant. This processing architecture traverses the queue of active rules as rule processing threads become available, the processing thread instantiates the rule based on the rule definition and rule state information removed from the queue of active rules, checks an event storage including sensor messages related to the monitored location, and either completes the rule processing or returns the rule to the end of the queue for additional processing later. This architecture is projected to scale better to millions of subscribers than instantiating every rule in a separate thread, for example millions of threads, and processing them until completion.

Figure 1:
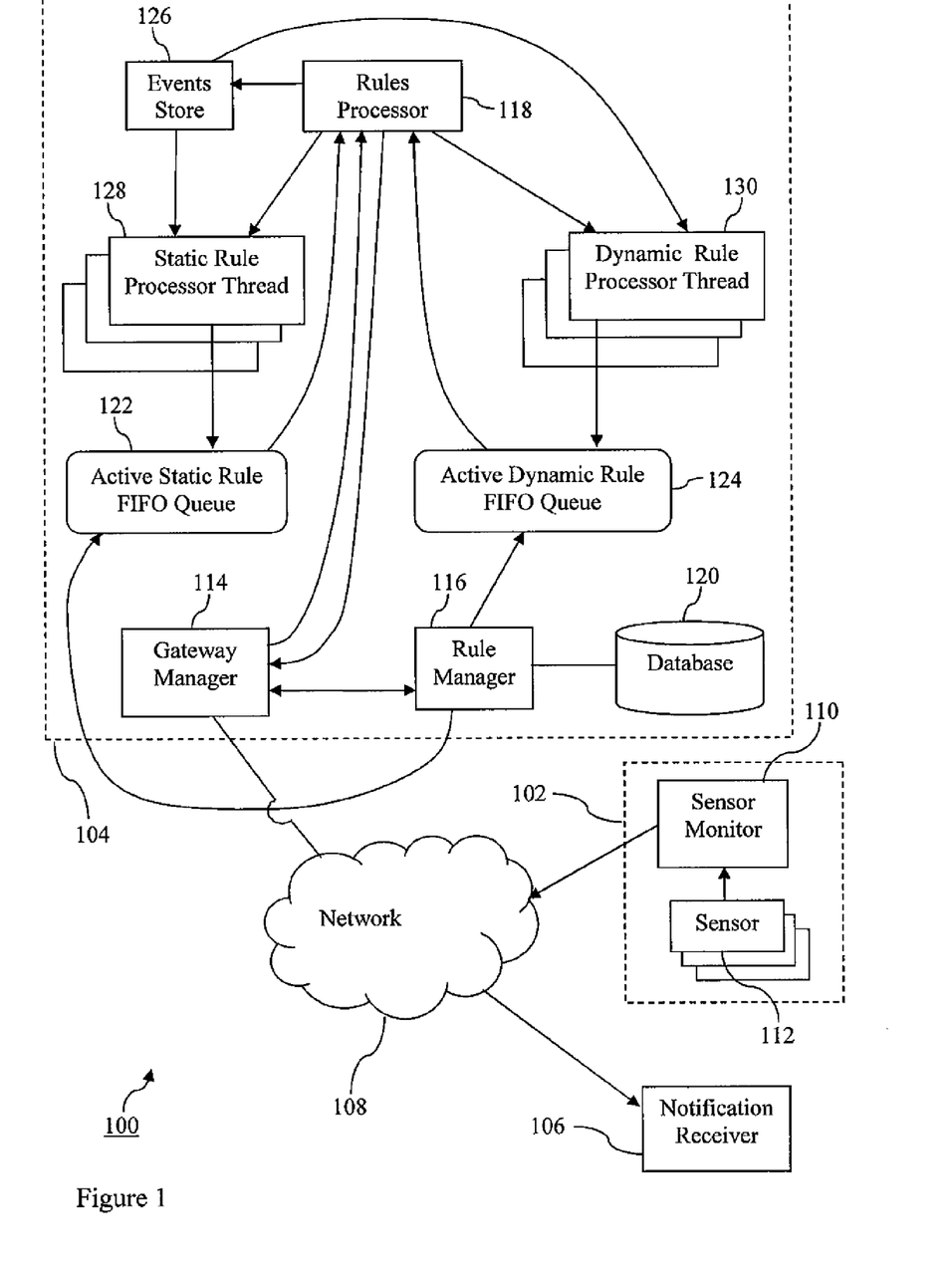
FIG. 1 is a block diagram of an event monitoring system according to an embodiment of the disclosure.

Turning now to FIG. 1, an embodiment of an events monitoring system 100 is shown. The events monitoring system 100 comprises a monitored location 102, an events monitoring server 104, and a notification receiver 106. While one monitored location 102 and one notification receiver 106 are depicted, it is to be understood that it is contemplated that the events monitoring system 100 may comprise a large number, for example several thousands or millions, of monitored locations 102 and notification receivers 106. The monitored location 102, the events monitoring server 104, and the notification receiver 106 communicate with one another through a network 108. In some embodiments the different monitored locations may be associated with different residences or buildings, while in other embodiments the different monitored locations may be distributed within a single large building, for example a manufacturing facility or an office building.

In an embodiment the monitored location 102 may be the private residence of an elderly person. The monitored location 102 includes a sensor monitor 110 that receives events from several sensors 112, for example motion sensors. The events may be a transition of a sensor detecting motion or the transition of a sensor detecting the opening or a door or a window, for example the opening of a refrigerator door. In an embodiment a sensor may be said to be TRUE if the sensor has generated an event. The sensor monitor 110 sends these events to the events monitoring server 104 via the network 108, for example using an email service where the subject line of the email message identifies an account number of an event monitoring system subscriber. The sensors 112 are placed appropriately throughout the monitored location 102 to determine that the resident, for example an elderly person, has risen in the morning and is generally moving about the monitored location 102 in an expected manner, for example entering the living room, traversing a room and entering a kitchen, opening a refrigerator door.

In some circumstances multiple sensors may be placed in a single large room or at opposite ends of a long hallway. Yet other dispositions and arrangements of sensors may be provided in some embodiments. The sensors may be motion sensors, vibration sensors, image sensors, or other types of sensors. One or more of the sensors may detect a chip or radio frequency identification tag carried by or embedded in the monitored entity or elderly person. The sensors may communicate with the sensor monitor 110 through wired or wireless communication links.

In an embodiment multiple sensor monitors 110 may be distributed throughout a building, for example within an manufacturing building or within an office building, with each sensor monitor 110 in communication with a modest number of sensors 112. Alternatively, one or a small number of sensor monitors 110 may be distributed within a building with each sensor monitor 110 in communication with a large number of sensors 112. It will be understood that the numbers of sensor monitors 110 and the numbers of sensors 112 linked to the sensor monitors 110 within a building is a design choice that depends upon individual installation circumstances and operational requirements. All of these structures are contemplated by the present disclosure.

The notification receiver 106 may be one or more general purpose computers, cell phones, personal data assistants (PDAs), or other electronics communication device configured to receive notifications from the events monitoring server 104. General purpose computer systems are discussed in greater detail hereinafter. Cell phones and PDAs are discussed in greater detail hereinafter. In an embodiment, the events monitoring server 104 may send messages associated with one monitored location 102 out to a plurality of notification receivers 106, for example to a computer of a first son, to a mobile phone of a second son, to a computer of a daughter, and to a PDA of a granddaughter of the monitored elderly person. The notifications may be sent by the events monitoring server 104 to the notification receiver 106 in a variety of formats including an email message, a simple message system (SMS) message, a text message, a pre-recorded voice message, a synthesized voice message, and other message format.

The network 108 is any of a public switched telephone network (PSTN), a public data network, and/or a combination of these.

The events monitoring server 104 may be implemented on any general purpose computer system that is configured to handle the processing load. General purpose computer systems are discussed in greater detail hereinafter. The events monitoring server 104 in an embodiment comprises a gateway manager 114, a rule manager 116, a rules processor 118, a database 120, an active static rule first-in first-out (FIFO) queue 122, an active dynamic rule FIFO queue 124, an events store 126, a plurality of static rule processor threads 128, and a plurality of dynamic rule processor threads 130. In different embodiments the events monitoring server 104 may include more or fewer components. In different embodiments two or more of the components shown to be part of the events monitoring server 104 may be combined into a single component.

The gateway manager 114 receives events sent by the monitored location 102 via the network 108 and sends notifications to the notification receiver 106 via the network 108. The gateway manager 114 forwards the events to the rule manager 116 and to the rules processor 118. The gateway manager 114 may generate various logs and send them to the database 120 for storage, including event logs, notification logs, and other logs. In an embodiment a mail server (not shown) may receive the events sent by the monitored location 102 via the network 108 and forward the events to the gateway manager 114. The mail server may receive notifications from the gateway manager 114 and forward the notifications to the notification receiver 106 via the network 108.

The rule manager 116 determines when static rules defined by entries in the database 120 become active, for example at an earliest daily monitoring time such as 7 AM which is the earliest Grandma is expected to rise, and adds or pushes an appropriate static rule definition and associated state information onto the active static rule FIFO queue 122. Similarly, the rule manager 116 determines when dynamic rules defined by entries in the database 120 are triggered by an appropriate event, for example by Grandma entering the bathroom, and adds or pushes an appropriate dynamic rule definition and state information onto the active static rule FIFO queue 122. Pushing rule definitions and rule state onto the active rule FIFO queue 122, 124 may be referred to as pushing a rule onto the queue 122, 124. Both static and dynamic rules will be discussed in greater detail hereinafter.

The rules processor 118 launches an effective number of static rule processor threads and an effective number of dynamic rule processor threads to handle the event processing load. A thread is short for "a thread of execution." Threads may be thought of as light weight processes, because threads are associated with less context than are processes, and hence context switching for threads is less involved and time consuming than context switching for processes.

The number of threads launched by the rules processor 118 may be determined by a configuration parameter of the events monitoring server 104, for example set by an application programming interface (API) or control panel (not shown) of the events monitoring server 104. Alternatively, the number of threads launched by the rules processor 118 may be determined automatically in response to changing event processing load. The event processing load may grow or decline according to daily trends, weekly trends, seasonal trends, as well as subscription trends.

The rules processor 118 places events received from the gateway manager 114 into the events store 126. The events store 126 may be any of a variety of data structures including queues, linked lists, rings, binary search trees, hash tables, and other data structures known to those skilled in the art. The data structures may be chosen to support efficient searching for events associated with a specific chain rule, for example associated based on an account number. The rules processor 118 grooms the events store 126 to remove expired events, for example events that are older than oldest rule or the least recently processed rule in either of the active static rule FIFO queue 122 and the active dynamic rule FIFO queue 124. Note that if the event is older than the oldest rule, this implies that the appropriate rules have already responded to the event and hence the event may be discarded. Grooming the events store 126 reduces search times and conserves memory resources. In an embodiment, the static rule processor threads 128 and the dynamic rule processor threads 130 may remove expired events, for example those events which associate to only one rule.

Each of the static rule processor threads 128 are instantiations of the same static rule processing code. Similarly, each of the dynamic rule processor threads 130 are instantiations of the same dynamic rule processing code. When one of the static rule processor threads 128 is idle, the rules processor 118 fetches or pops a rule off of the active static rule FIFO queue 122 and provides this rule to the one of the static rule processor threads 128 that is idle. In an embodiment, there may be a parameter associated with static rules that assure that the static rule remains on the active static rule FIFO queue 122 for a minimum time duration, for example for a minimum of one minute, for a minimum of five minutes, or for some other effective minimum time duration. Providing a minimum time duration that a static rule remains on the active static rule FIFO queue 122 may promote effective utilization of processing resources. Popping a rule off of the active rule FIFO queue 122, 124 may involve removing both a definition of the rule and any state associated with the rule. The rule, as discussed in more detail hereinafter, may define a linked or chained group of rules for responding to sensor events.

The static rule processor thread 128 searches the events store 126 for an event associated with the rule. If there is no associated event and if a completion time limit associated with the rule has not passed, the static rule processor thread 128 may return the rule to the active static rule FIFO queue 122 for processing again at a later time. If the completion time limit associated with the rule has passed, the static rule processor thread 128 may send a negative notification message defined by the rule to the rules processor 118, the rules processor 118 sends the negative notification message to the gateway manager 114, and the gateway manager 114 sends the negative notification message, for example "grandma has not risen from bed this morning," to the notification receiver 106.

If the static rule processor thread 128 finds an event associated with the rule, the static rule processor thread 128 processes the event in accordance with the rule, for example marking the status of one of several event chain steps or gates as "TRUE" or completed. This may also be referred to as marking the status of a rule, for example one of multiple rules all associated with the same chain rule, as "COMPLETED." If the static rule processor thread 128 determines that all of the event chain rule steps or gates are completed, the static rule processor thread 128 may mark the status of the event chain rule completed and sends a positive notification message to the notification receiver 106 through the series of the rules processor 118 and the gateway manager 114 as described above, for example sending a "grandma is up and about this morning" message. The static rule processor thread 128 does not return the rule to the active static rule FIFO queue 122 when the rule is complete.

When one of the dynamic rule processor threads 130 is idle, the rules processor 118 fetches or pops a rule off of the active dynamic rule FIFO queue 124 and provides this rule to the one of the dynamic rule processor threads 130 that is idle. In an embodiment, there may be a parameter associated with dynamic rules that assure that the dynamic rule remains on the active dynamic rule FIFO queue 124 for a minimum time duration, for example for a minimum of one minute, for a minimum of five minutes, or for some other effective minimum time duration. Providing a minimum time duration that a dynamic rule remains on the active dynamic rule FIFO queue 124 may promote effective utilization of processing resources. The processing of the rules by the dynamic rule processor threads 130 is similar to that of the static rule processor threads 128. The dynamic rule processor thread 130 searches the events store 126 for an event associated with the rule. If there is no associated event and if a completion time limit associated with the rule has not passed, the dynamic rule processor thread 130 may return the rule to the active dynamic rule FIFO queue 124 for processing again at a later time.

Time limits associated with dynamic rules are linked to a time of the trigger event associated with the dynamic rule. For example, if a first dynamic rule is linked to the trigger event of motion in the bathroom, and if grandma enters the bathroom at 1:33 PM, time limits associated with the first dynamic rule are relative to 1:33 PM. For example, a bedroom motion rule portion of the first dynamic rule may include a duration of 30 minutes, a step message start time of 15 minutes, and a step interval of 5 minutes. In this exemplary case, if motion is not detected in the bedroom within 15 minutes after the trigger event, for example by 1:48 PM, the dynamic rule processor threads 130 sends a first step notification message to the notification receiver 106 through the intermediary of the rules processor 118 and the gateway manager 114. The step notification message may be "grandma has entered and remains in the bathroom." If motion in the bedroom is not detected this step notification message is repeatedly sent at the time intervals defined by the step interval, for example every 5 minutes at 1:53 PM and 1:58 PM. If motion in the bedroom is not detected within the duration, for example 30 minutes after 1:33 PM or 2:03 PM, the dynamic rule processor threads 130 sends a negative notification message to the notification receiver 106 through the intermediary of the rules processor 118 and the gateway manager 114, for example "grandma has entered the bathroom and has not exited for an excessive time duration."

It is contemplated that some dynamic rules may be defined to have zero time duration, which would typically have the effect that when such a zero time duration dynamic rule is triggered by the associated trigger event that the associated notification would be immediately sent. This processing behavior may be desirable for some events, such as the opening of a window which may signal a forced entry has occurred. In an embodiment, a zero time duration dynamic rule may be conditioned on one or more preceding dynamic rules within an associated rule chain, for example preceding rules which collectively are associated with the resident leaving their home or the resident retiring for sleep.

If the dynamic rule processor thread 130 finds an event associated with the rule, the dynamic rule processor thread 130 processes the event in accordance with the rule, for example marking the status of one of several event chain steps or gates as "TRUE" or completed. If the dynamic rule processor thread 130 determines that all of the event chain rule steps or gates are completed, the dynamic rule processor thread 130 may mark the status of the event chain rule completed and sends a positive notification message to the notification receiver 106 through the series of the rules processor 118 and the gateway manager 114 as described above, for example sending a "grandma has exited the bathroom and resumed other activities." The dynamic rule processor thread 130 does not return the rule to the active dynamic rule FIFO queue 124 when the rule is complete.

To promote flexibility and ease of engaging with new subscribers, the functionality provided by the events monitoring server 104 for any particular monitored location 102 may be defined by entries in tables in the database 120. These tables may include, for example, a rule chain table, a static rule table, a dynamic rule table, and a rule sensor table. By changing or updating these table entries, the event monitoring functionality of the events monitoring server 104 may be changed. This may be referred to as a data driven application. This capability may allow for easy addition of new subscribers to the events monitoring system 100.

A rule chain, generally, may be composed from multiple entries in the rule chain table which share a common account number and a common rule chain identifier. The rule chain associates one or more rules together to provide an event monitoring sequence of interest. Each entry in the rule chain table identifies a rule that is defined in either the static rule table or the dynamic rule table. The rule chain entry may define the positive notification message that is to be sent when the rule chain or the event monitoring sequence completes successfully.

For example, a daughter may wish to confirm that her elderly mother (1) rises from bed, as evidenced by motion detected by one of two motion sensors in a bedroom, between 7 AM and 8 AM as defined by a first static rule; (2) moves about a living room area, as evidenced by motion detected by a motion sensor in the living room, between 7:30 AM and 9 AM as defined by a second static rule; and (3) opens a refrigerator door, as evidenced by a sensor associated with the refrigerator door, between 9 AM and 10 AM as defined by a third static rule. When the three events monitored by the three static rules complete successfully, the positive notification message "mother is up and about" may be sent to the daughter. A rule chain that associates the first static rule, the second static rule, and the third static rule may be defined by creating three appropriate entries in the rule chain table. An embodiment of an exemplary format for entries in the rule chain table is represented in the form of a SQL command below.

```
CREATE TABLE rule_chain (
acct_id VARCHAR(20) NOT NULL,
chain_name VARCHAR(25) NOT NULL,
rule_name VARCHAR(25) NOT NULL,
trigger_sensor VARCHAR(20),
positive_message VARCHAR(100),
PRIMARY KEY (acct_id, chain_name, rule_name))
;
```

Note that in other embodiments other fields may be included in the rule chain table and fields may be formatted differently than expressed above.

A static rule, generally, may be defined by an entry in the static rule table and by one or more associated entries in the rule sensor table. The static rule is associated with one or more rule chains by a static rule name or identifier and by an account or customer identifier. One or more sensor rules are associated with the static rule by including the static rule name or identifier in the sensor rule entries in the rule sensor table, as discussed below. The static rule may define a start time and an end time for processing the static rule.

The static rule may define a gated function to promote monitoring events generated by more than one sensor. The gated function defines how the rule is to combine the states of the monitored sensors, when appropriate. The static rule may be said to define or specify a condition, which may be the combination of time limit conditions and gated function conditions. If only one sensor is monitored by a static rule, the gated function field may contain the NOT NULL value. An embodiment of an exemplary format for entries in the static rule table is represented in the form of a SQL command below.

```
CREATE TABLE static_time_rule (
acct_id VARCHAR(20) NOT NULL,
rule_name VARCHAR(25) NOT NULL,
start_time TIME NOT NULL,
end_time TIME NOT NULL,
gate CHAR(1) default ',St' NOT NULL,
negative_message VARCHAR(100),
```

PRIMARY KEY (acct_id, rule_name))
;
Note that in other embodiments other fields may be included in the static rule table and fields may be formatted differently than expressed above.

A dynamic rule, generally, may be defined by an entry in the dynamic rule table and by one or more associated entries in the rule sensor table. The dynamic rule is associated with one or more rule chains by a dynamic rule name or identifier and by an account or customer identifier. One or more sensor rules are associated with the dynamic rule by including the dynamic rule name or identifier in the sensor rule entries in the rule sensor table, as discussed below. The dynamic rule may define a duration and other timing parameters. As noted above, in some circumstances a zero time duration may be suitable in some monitoring situations. The dynamic rule defines a gated function to promote monitoring events generated by more than one sensor. The dynamic rule may be said to define or specify a condition, which may be the combination of time limit conditions, for example the duration and step values, and gated function conditions. An embodiment of an exemplary format for entries in the dynamic rule table is represented in the form of a SQL command below.

CREATE TABLE dynamic_time_rule (
acct_id VARCHAR(20) NOT NULL,
rule_name VARCHAR(25) NOT NULL,
duration INT NOT NULL,
time_unit VARCHAR(5) default 'hours' NOT NULL,
gated CHAR(1) default '&' NOT NULL,
step_message VARCHAR(100),
step-start VARCHAR(5),
step VARCHAR(5),
negative_message VARCHAR(100),
next_rule_name VARCHAR(25),
PRIMARY KEY (acct_id, rule_name))
;
Note that in other embodiments other fields may be included in the dynamic rule table and fields may be formatted differently than expressed above.

A sensor rule, generally, may be defined in the rule sensor table. The sensor rule is associated with a static rule or a dynamic rule by an account or customer identifier and by the name of the static or dynamic rule. The sensor rule may identify a sensor type and an operator that indicates what condition causes the sensor to be TRUE. An embodiment of an exemplary format for entries in the sensor rule table is represented in the form of a SQL command below.

CREATE TABLE rule_sensor (
acct_id VARCHAR(20) NOT NULL,
rule_name VARCHAR(25) NOT NULL,
sensor_name VARCHAR(25) NOT NULL,
sensor_type VARCHAR(25) NOT NULL,
status VARCHAR(10) NOT NULL,
operator CHAR(2),
PRIMARY KEY (acct_id, rule_name, sensor_name))
;
Note that in other embodiments other fields may be included in the rule sensor table and fields may be formatted differently than expressed above.

Figure 2:
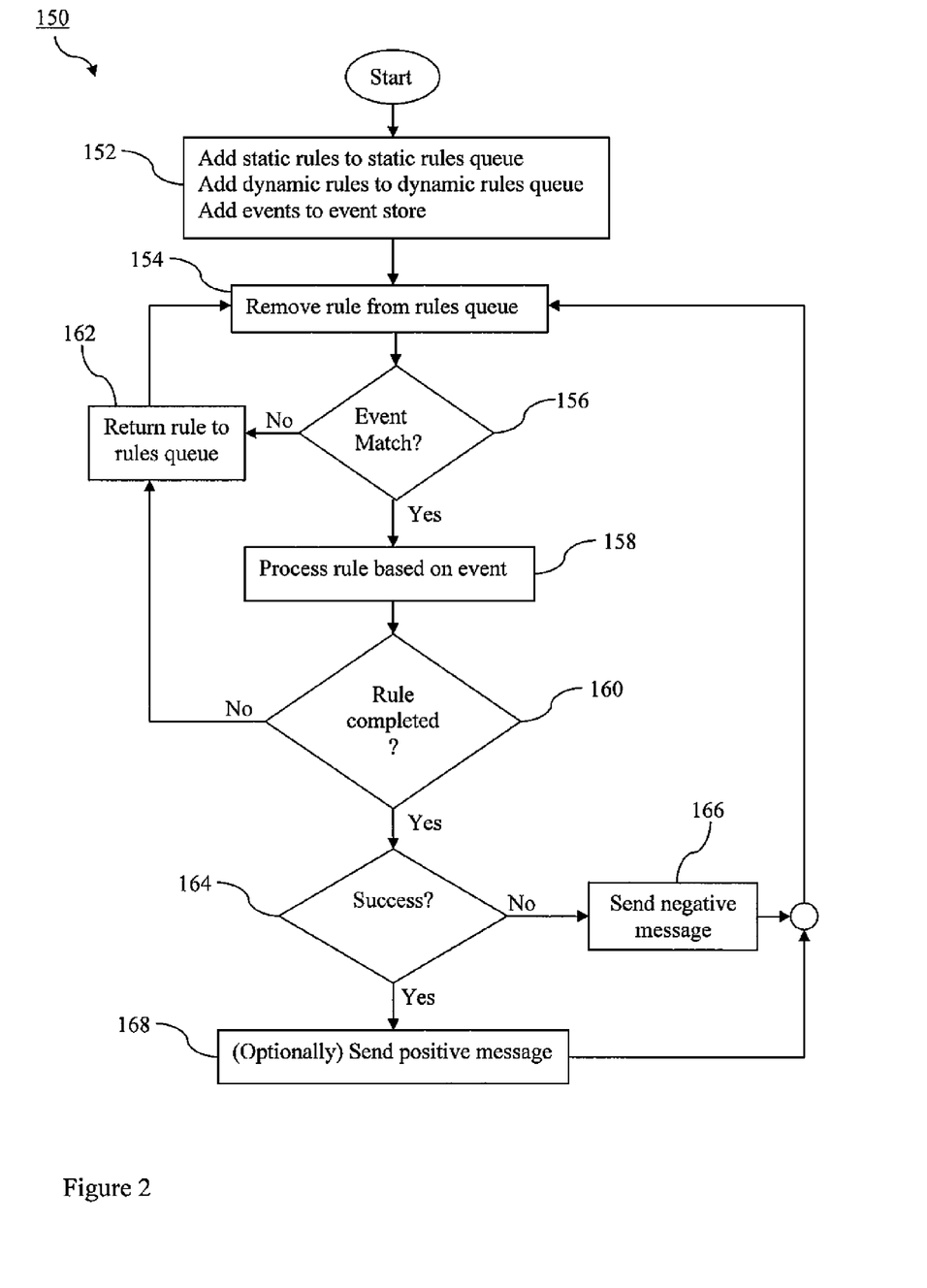
FIG. 2 is a flow diagram of a method according to an embodiment of the disclosure.

Turning now to FIG. 2, a method 150 is described that may be performed by at least some of the components of the events monitoring server 104. In block 152 static rules are added to the static rules queue 122, dynamic rules are added to the dynamic rules queue 124, and events are added to the events store 126. The static and dynamic rules may be added to the rules queues 122, 124 at different times. For example, the static rules may be added to the static rules queue 122 at the start time identified in an associated static rule table entry, and the dynamic rule may be added to the dynamic rules queue 124 at the time that the trigger event identified in an associated chain rule table entry is received. The events are added to the events store 126 at the times they are received.

In block 154 a rule definition and associated state information is removed from one of the rules queues 122, 124. The rule definition may identify a rule chain including a description of one or more rules and one or more sensors. In block 156 the pending events, for example events in the event store 126, are checked to see if an event related to the rule is present, for example by matching an account id and a rule name associated with the event with an account id and a rule name associated with the rule. If there is a match between a pending event and the rule, in block 158 the rule is processed based on the event, for example the rule may be processed by one of the processor threads 128, 130. If the event indicates that a sensor is TRUE, the associated rule may be given the status of TRUE, for example a bedroom motion rule may be given the status of TRUE when an associated bedroom sensor event is matched. In block 160 the rule may be completed because the rule timed out, the failure case, or because all of the events associated with the rule had completed as expected, the success case. In block 164, if the rule chain is completed successfully, in block 168, an optional positive notification message is sent. Otherwise, in block 164, if the rule chain completes without success, in block 166 a negative message is sent. For some dynamic rules sending a positive notification message is not mandatory but only optional.

In block 156 if there is no pending event that matches the rule, in block 162 the rule definition and state information are returned to the rules queue 122, 124 for more processing at a later time. In block 160, similarly, if the rule is not completed, in block 162 the rule definition and state information are returned to the rules queue 122, 124 for more processing at a later time.

An example scenario will be discussed to further illustrate the method 150. At 7 AM a static rule for bedroom motion may be added to the static rules queue 122. The static rule for bedroom motion is periodically removed from the static rules queue 122 and the events store 126 is searched for a bedroom motion sensor event. Not finding the bedroom motion sensor event on the events store 126, the static rule for bedroom motion is returned to the end of the static rules queue 122. At 7:30 AM a static rule for common area motion, for example motion in a living room area, may be added to the static rules queue 122. The static rule for common area motion is periodically removed from the static rules queue 122 and the events store 126 is searched for a common area motion sensor event. Not finding the common area motion sensor event on the events store 126, the static rule for common area motion is returned to the end of the static rules queue 122.

At 7:40 AM a bedroom motion event is received and added to the events store 126. At some later time, the static rule for bedroom motion is removed from the static rules queue 122 and the events store 126 is searched for a bedroom motion event. The bedroom motion event is found on the events store 126, the static rule for bedroom motion is set to a TRUE value and returned to the static rules queue 122. The bedroom motion event is deleted from the events store 126.

At 7:50 AM a common area motion event is received and added to the events store 126. At some later time, the static rule for common area motion is removed from the static rules queue 122 and the events store 126 is searched for a common area motion event. The common area motion event is found on the events store 126, the static rule for common area motion is set to a TRUE value and returned to the static rules queue 122. The common area motion event is deleted from the events store 126. If the static rule for bedroom motion and the static rule for common area motion form a complete rule chain, on completion of both the static rule for bedroom motion and the static rule for common area motion, before time outs associated with each static rule, a positive message is sent to a subscriber, for example a "grandma is up and about in her house" message via email to a granddaughter. The static rules for bedroom motion and for common area motion are removed from the static rules queue 122.

In another scenario, if the static rule for common area motion has an expiration time of 8 AM and the static rule for common area motion has not been deemed TRUE before 8 AM, for example if no common area motion event has been received and stored in the events store 126 before 8 AM, the static rule for common area motion is set FALSE and a negative message defined in the static rule for common area motion is sent to a subscriber, for example a "grandma did not move through the common area" message via email to the granddaughter.

Continuing with the primary example scenario, when a bathroom motion sensor event is received, a dynamic rule for bedroom motion may be added to the dynamic rules queue 124 and an associated bedroom motion timer is initiated. At some later time, the dynamic rule for bedroom motion is removed from the dynamic rules queue 124 and the events store 126 is searched for a bedroom motion event. Not finding the bedroom motion event on the events store 126, the dynamic rule for bedroom motion is returned to the end of the dynamic rules queue 124.

A bedroom motion event is received and placed in the events store 126. When the dynamic rule for bedroom motion is removed from the dynamic rules queue 124 for processing, the associated bedroom motion event is found in the events store 126. The bedroom motion event is removed from the events store 126, the dynamic rule for bedroom motion is set to TRUE and returned to the dynamic rules queue 124, and a dynamic rule for hallway motion, which may be sequentially linked with the dynamic rule for bedroom motion, is added to the dynamic rules queue 124 and an associated hallway motion timer is initiated. If the timer associated with the dynamic rule for bedroom motion expires before the bedroom motion event is received, a negative message is sent to the subscriber, for example a "grandma has been in the bathroom for an excessive amount of time" message emailed to the granddaughter.

At some later time, the dynamic rule for hallway motion is removed from the dynamic rules queue 124 and the events store 126 is searched for a hallway motion event. Not finding the hallway motion event on the events store 126, the dynamic rule for hallway motion is returned to the end of the dynamic rules queue 124.

A hallway motion event is received and placed in the events store 126. When the dynamic rule for hallway motion is removed from the dynamic rules queue 124 for processing, the associated hallway motion event is found in the events store 126, the dynamic rule for hallway motion is set to TRUE and returned to the dynamic rules queue 124. The hallway motion event is removed from the events store 126. If the dynamic rules for bedroom motion and hallway motion form a complete dynamic rule chain, a positive message may be sent out to a subscriber, for example "grandma has entered and left the bathroom" to the granddaughter. No message is necessary, however, and whether a message is sent or not sent is a matter of how the rule chain for monitoring the bathroom is defined by the subscriber. Some subscribers may wish to receive a notification of grandma leaving the bathroom, but other subscribers may only wish to receive a notification if grandma does not leave the bathroom in a timely interval.

If the timer associated with the dynamic rule for hallway motion expires before the hallway motion event is received, a negative message may be sent to the subscriber, for example a "grandma used the bathroom and then entered the bedroom but has not exited the bedroom for an excessive amount of time" message emailed to the granddaughter. Using other rule chain definitions different subscribers can define a monitoring scenario that suits their monitoring needs. While a system monitoring the movements of an elderly woman has been described in the example scenario above, one skilled in the art will readily appreciate that the system 100 may be used to monitor other buildings and/or dwellings. Also, while a single monitored location was the focus of the example scenario above, it should be understood that events and rules from a plurality of separate buildings and/or dwellings associated with a plurality of subscribers will be entered into the events store 126, the static rules queue 122, and the dynamic rules queue 124. While an extended scenario has been described above, in some embodiments events and rules may be processed differently.

Figure 3:
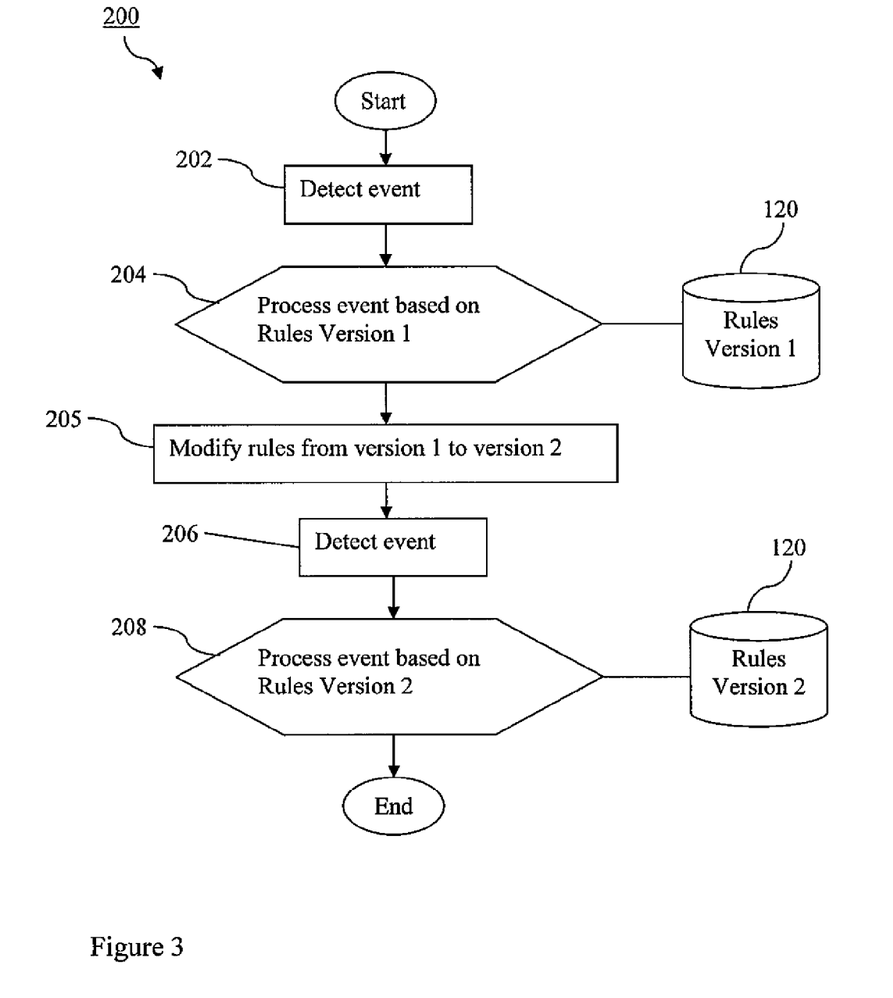
FIG. 3 is a flow diagram of another method according to an embodiment of the disclosure.

Turning now to FIG. 3 a method 200 of providing elder care is described. In block 202 motion is detected at a monitored location, for example in a bedroom of an elderly mother of an events monitoring subscriber. In block 204 the motion event is processed based on a first version of rules stored in the database 120. For example the event monitoring rules associated with the elderly mother may be defined in a series of entries in a chain rule table, in a dynamic rules table, in a static rules table, and in a sensor rules table, wherein all the entries of the several tables are associated at least by a common account identification number. The processing may lead to sending a "mother is up and about" message to the events monitoring subscriber.

In block 205 the event monitoring rules associated with the elderly mother are changed or updated to a second version. Because the rules are defined by entries in database tables, the rules are changed simply by revising the database tables. No computer programs need be recompiled to bring the changed event monitoring functionality into effect, no virtual machine need be restarted. In block 206 motion is detected at the monitored location of the elderly mother, for example the next morning. In block 208 the motion event is processed based on the second version of rules stored in the database 120. The processing according to the second version or rules may lead to sending a "mother is up and about and has accessed the refrigerator this morning" message to the events monitoring subscriber.

Figure 4:
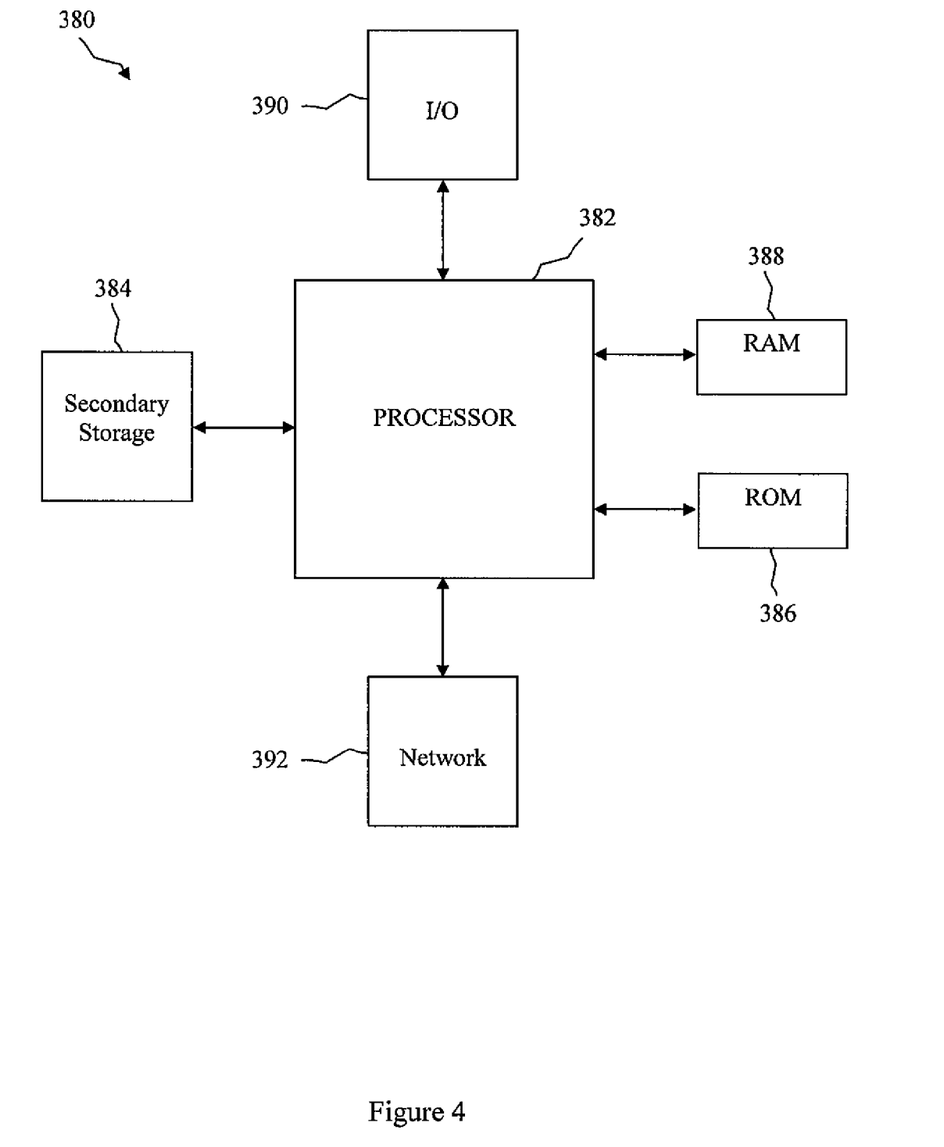
FIG. 4 illustrates an exemplary general purpose computer system suitable for implementing the several embodiments of the disclosure.

Portions of the events monitoring system 100 described above may be implemented on any general-purpose computer with sufficient processing power, memory resources, and network throughput capability to handle the necessary workload placed upon it. For example, in an embodiment the events monitoring server 104 and the sensor monitor 110 may be general-purpose computers. In an embodiment, the notification receiver 106 may be a general-purpose computer or it may be a mobile device such as a mobile phone or PDA. FIG. 4 illustrates a typical, general-purpose computer system suitable for implementing one or more embodiments disclosed herein. The computer system 380 includes a processor 382 (which may be referred to as a central processor unit or CPU) that is in communication with memory devices including secondary storage 384, read only memory (ROM) 386, random access memory (RAM) 388, input/output (I/O) devices 390, and network connectivity devices 392. The processor may be implemented as one or more CPU chips.

The secondary storage 384 is typically comprised of one or more disk drives or tape drives and is used for non-volatile storage of data and as an over-flow data storage device if RAM 388 is not large enough to hold all working data. Secondary storage 384 may be used to store programs which are loaded into RAM 388 when such programs are selected for execution. The ROM 386 is used to store instructions and perhaps data which are read during program execution. ROM 386 is a non-volatile memory device which typically has a small memory capacity relative to the larger memory capacity of secondary storage. The RAM 388 is used to store volatile data and perhaps to store instructions. Access to both ROM 386 and RAM 388 is typically faster than to secondary storage 384.

I/O devices 390 may include printers, video monitors, liquid crystal displays (LCDs), touch screen displays, keyboards, keypads, switches, dials, mice, track balls, voice recognizers, card readers, paper tape readers, or other well-known input devices. The network connectivity devices 392 may take the form of modems, modem banks, ethernet cards, universal serial bus (USB) interface cards, serial interfaces, token ring cards, fiber distributed data interface (FDDI) cards, wireless local area network (WLAN) cards, radio transceiver cards such as code division multiple access (CDMA) and/or global system for mobile communications (GSM) radio transceiver cards, and other well-known network devices. These network connectivity devices 392 may enable the processor 382 to communicate with an Internet or one or more intranets. With such a network connection, it is contemplated that the processor 382 might receive information from the network, or might output information to the network in the course of performing the above-described method steps. Such information, which is often represented as a sequence of instructions to be executed using processor 382, may be received from and outputted to the network, for example, in the form of a computer data signal embodied in a carrier wave Such information, which may include data or instructions to be executed using processor 382 for example, may be received from and outputted to the network, for example, in the form of a computer data baseband signal or signal embodied in a carrier wave. The baseband signal or signal embodied in the carrier wave generated by the network connectivity devices 392 may propagate in or on the surface of electrical conductors, in coaxial cables, in waveguides, in optical media, for example optical fiber, or in the air or free space. The information contained in the baseband signal or signal embedded in the carrier wave may be ordered according to different sequences, as may be desirable for either processing or generating the information or transmitting or receiving the information. The baseband signal or signal embedded in the carrier wave, or other types of signals currently used or hereafter developed, referred to herein as the transmission medium, may be generated according to several methods well known to one skilled in the art.

The processor 382 executes instructions, codes, computer programs, scripts which it accesses from hard disk, floppy disk, optical disk (these various disk based systems may all be considered secondary storage 384), ROM 386, RAM 388, or the network connectivity devices 392.

Figure 5:
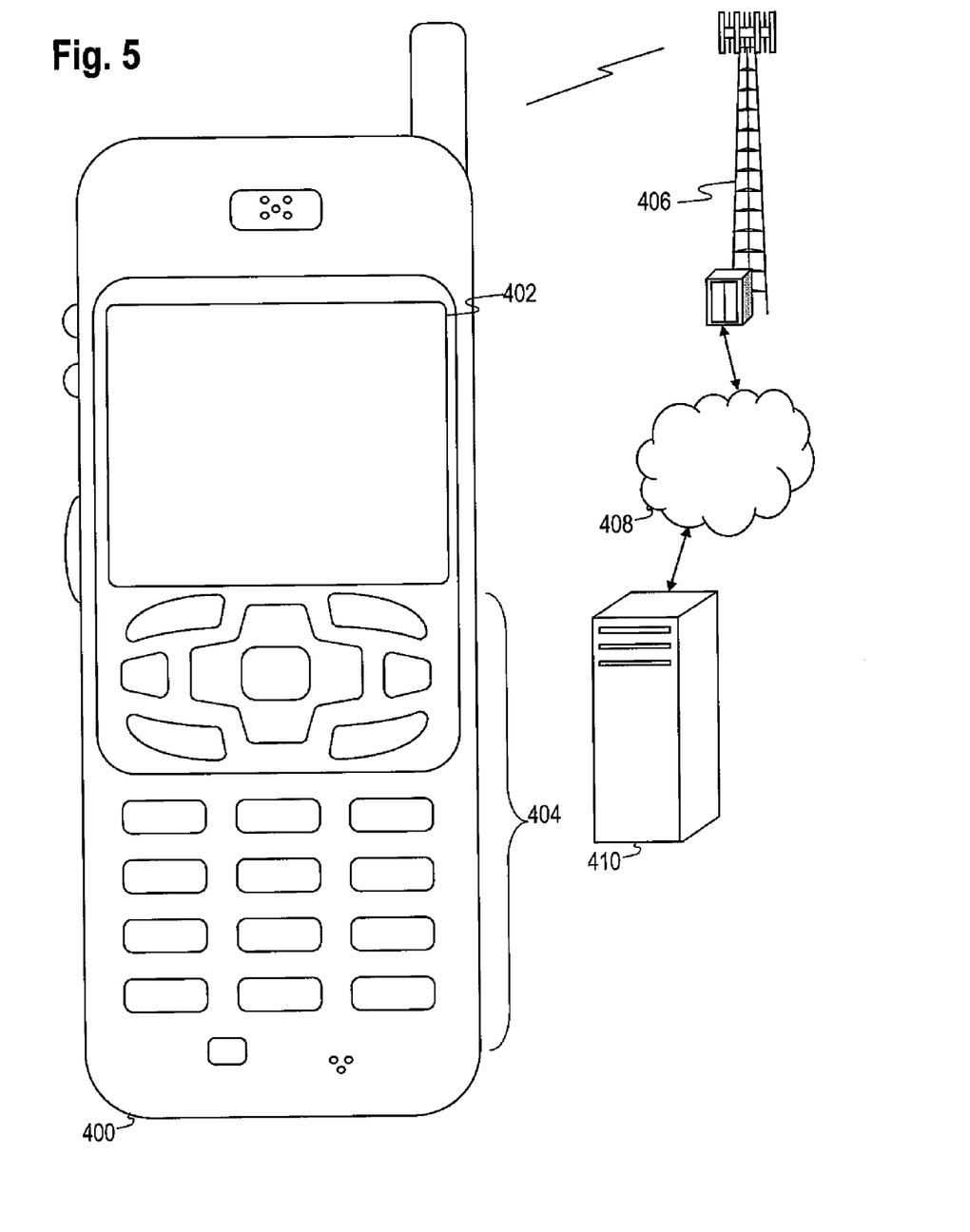
FIG. 5 is an illustration of a mobile device according to an embodiment of the disclosure.

FIG. 5 shows a wireless communications system including the handset 400. FIG. 5 depicts the handset 400, which is operable for implementing aspects of the present disclosure, but the present disclosure should not be limited to these implementations. In an embodiment, for example, the notification receiver 106 may be implemented as the handset 400. Though illustrated as a mobile phone, the handset 400 may take various forms including a wireless handset, a pager, a personal digital assistant (PDA), a portable computer, a tablet computer, or a laptop computer. Many suitable handsets combine some or all of these functions. In some embodiments of the present disclosure, the handset 400 is not a general purpose computing device like a portable, laptop or tablet computer, but rather is a special-purpose communications device such as a mobile phone, wireless handset, pager, or PDA. The handset 400 may support specialized work assignments such as inventory control, job control, and/or task management functions.

The handset 400 includes a display 402 and a touch-sensitive surface or keys 404 for input by a user. The handset 400 may present options for the user to select, controls for the user to actuate, and/or cursors or other indicators for the user to direct. The handset 400 may further accept data entry from the user, including numbers to dial or various parameter values for configuring the operation of the handset. The handset 400 may further execute one or more software or firmware applications in response to user commands. These applications may configure the handset 400 to perform various customized functions in response to user interaction. Additionally, the handset 400 may be programmed and/or configured over-the-air, for example from a wireless base station, a wireless access point, or a peer handset 400.

The handset 400 may execute a web browser application which enables the display 402 to show a web page. The web page may be obtained via wireless communications with a cell tower 406, a wireless network access node, a peer handset 400 or any other wireless communication network or system. The cell tower 406 (or wireless network access node) is coupled to a wired network 408, such as the Internet. Via the wireless link and the wired network, the handset 400 has access to information on various servers, such as a server 410. The server 410 may provide content that may be shown on the display 402. Alternately, the handset 400 may access the cell tower 406 through a peer handset 400 acting as an intermediary, in a relay type or hop type of connection.

Figure 6:
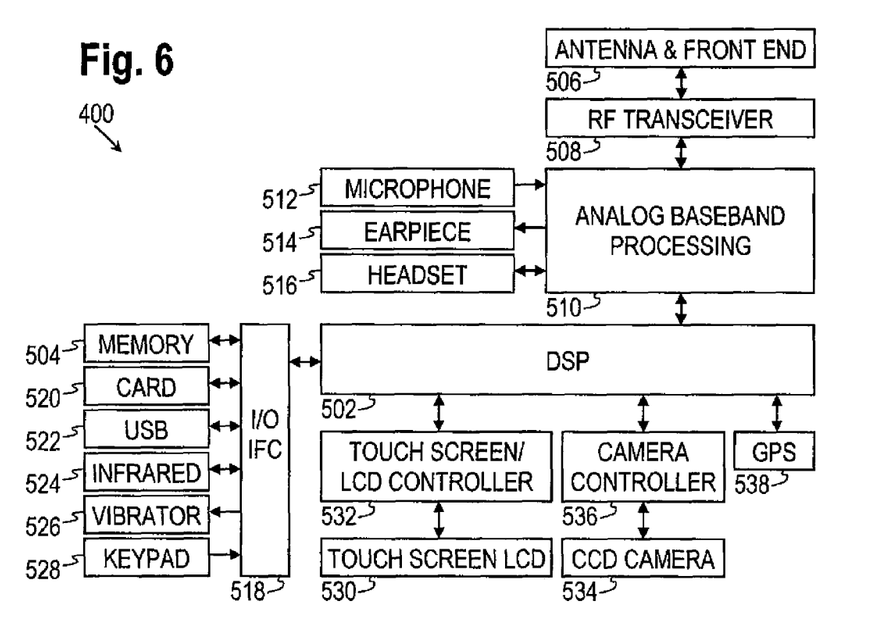
FIG. 6 is a block diagram of a mobile device according to an embodiment of the disclosure.

FIG. 6 shows a block diagram of the handset 400. While a variety of known components of handsets 400 are depicted, in an embodiment a subset of the listed components and/or additional components not listed may be included in the handset 400. The handset 400 includes a digital signal processor (DSP) 502 and a memory 504. As shown, the handset 400 may further include an antenna and front end unit 506, a radio frequency (RF) transceiver 508, an analog baseband processing unit 510, a microphone 512, an earpiece speaker 514, a headset port 516, an input/output interface 518, a removable memory card 520, a universal serial bus (USB) port 522, an infrared port 524, a vibrator 526, a keypad 528, a touch screen liquid crystal display (LCD) with a touch sensitive surface 530, a touch screen/LCD controller 532, a charge-coupled device (CCD) camera 534, a camera controller 536, and a global positioning system (GPS) sensor 538. In an embodiment, the handset 400 may include another kind of display that does not provide a touch sensitive screen. In an embodiment, the DSP 502 may communicate directly with the memory 504 without passing through the input/output interface 518.

The DSP 502 or some other form of controller or central processing unit operates to control the various components of the handset 400 in accordance with embedded software or firmware stored in memory 504 or stored in memory contained within the DSP 502 itself. In addition to the embedded software or firmware, the DSP 502 may execute other applications stored in the memory 504 or made available via information carrier media such as portable data storage media like the removable memory card 520 or via wired or wireless network communications. The application software may comprise a compiled set of machine-readable instructions that configure the DSP 502 to provide the desired functionality, or the application software may be high-level software instructions to be processed by an interpreter or compiler to indirectly configure the DSP 502.

The antenna and front end unit 506 may be provided to convert between wireless signals and electrical signals, enabling the handset 400 to send and receive information from a cellular network or some other available wireless communications network or from a peer handset 400. In an embodiment, the antenna and front end unit 506 may include multiple antennas whereby to support beam forming and/or multiple input multiple output (MIMO) operations. As is known to those skilled in the art, MIMO operations may provide spatial diversity which can be used to overcome difficult channel conditions and/or increase channel throughput. The antenna and front end unit 506 may include antenna tuning and/or impedance matching components, RF power amplifiers, and/or low noise amplifiers.

The RF transceiver 508 provides frequency shifting, converting received RF signals to baseband and converting baseband transmit signals to RF. In some descriptions a radio transceiver or RF transceiver may be understood to include other signal processing functionality such as modulation/demodulation, coding/decoding, interleaving/deinterleaving, spreading/despreading, inverse fast fourier transforming (IFFT)/fast fourier transforming (FFT), cyclic prefix appending/removal, and other signal processing functions. For the purposes of clarity the description here separates the description of this signal processing from the RF and/or radio stage and conceptually allocates that signal processing to the analog baseband processing unit 510 and/or the DSP 502 or other central processing unit. In some embodiments the RF transceiver 508, portions of the antenna and front end 506, the analog baseband processing unit 510 may be combined in one or more processing units and/or application specific integrated circuits (ASICs).

The analog baseband processing unit 510 may provide various analog processing of inputs and outputs, for example analog processing of inputs from the microphone 512 and the headset port 516 and outputs to the earpiece speaker 514 and the headset port 516. To that end, the analog baseband processing unit 510 may have ports for connecting to the built-in microphone 512 and the earpiece speaker 514 that enable the handset 400 to be used as a cell phone. The analog baseband processing unit 510 may further include a port for connecting to a headset or other hands-free microphone and speaker configuration. The analog baseband processing unit 510 may provide digital-to-analog conversion in one signal direction and analog-to-digital conversion in the opposing signal direction. In some embodiments at least some of the functionality of the analog baseband processing unit 510 may be provided by digital processing components, for example by the DSP 502 or by other central processing units.

The DSP 502 may perform modulation/demodulation, coding/decoding, interleaving/deinterleaving, spreading/despreading, inverse fast fourier transforming (IFFT)/fast fourier transforming (FFT), cyclic prefix appending/removal, and other signal processing functions associated with wireless communications. In an embodiment, for example in a code division multiple access (CDMA) technology application, for a transmitter function the DSP 502 may perform modulation, coding, interleaving, and spreading and for a receiver function the DSP 502 may perform despreading, deinterleaving, decoding, and demodulation. In another embodiment, for example in an orthogonal frequency division multiplex access (OFDMA) technology application, for the transmitter function the DSP 502 may perform modulation, coding, interleaving, inverse fast fourier transforming, and cyclic prefix appending and for a receiver function the DSP 502 may perform cyclic prefix removal, fast fourier transforming, deinterleaving, decoding, and demodulation. In other wireless technology applications yet other signal processing functions and combinations of signal processing functions may be performed by the DSP 502.

The DSP 502 may communicate with a wireless network via the analog baseband processing unit 510. In some embodiments, the communication may provide Internet connectivity, enabling a user to gain access to content on the Internet and to send and receive e-mail or text messages. The input/output interface 518 interconnects the DSP 502 and various memories and interfaces. The memory 504 and the removable memory card 520 may provide software and data to configure the operation of the DSP 502. Among the interfaces may be the USB port 522 and the infrared port 524. The USB port 522 may enable the handset 400 to function as a peripheral device to exchange information with a personal computer or other computer system. The infrared port 524 and other optional ports such as a Bluetooth interface or an IEEE 802.11 compliant wireless interface may enable the handset 400 to communicate wirelessly with other nearby handsets and/or wireless base stations.

The input/output interface 518 may further connect the DSP 502 to the vibrator 526 that, when triggered, causes the handset 400 to vibrate. The vibrator 526 may serve as a mechanism for silently alerting the user to any of various events such as an incoming call, a new text message, and an appointment reminder.

The keypad 528 couples to the DSP 502 via the I/O interface 518 to provide one mechanism for the user to make selections, enter information, and otherwise provide input to the handset 400. Another input mechanism may be the touch screen LCD 530, which may also display text and/or graphics to the user. The touch screen LCD controller 532 couples the DSP 502 to the touch screen LCD 530.

The CCD camera 534 enables the handset 400 to take digital pictures. The DSP 502 communicates with the CCD camera 534 via the camera controller 536. The GPS sensor 538 is coupled to the DSP 502 to decode global positioning system signals, thereby enabling the handset 400 to determine its position. In another embodiment, a camera operating according to a technology different from Charge Coupled Device cameras may be employed. Various other peripherals may also be included to provide additional functions, e.g., radio and television reception.

Figure 7:
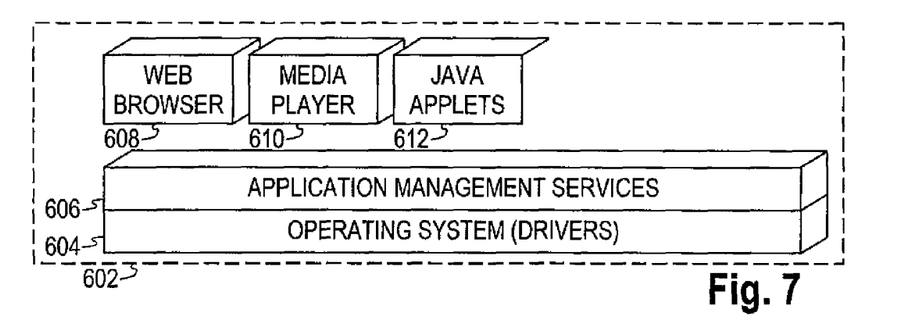
FIG. 7 is a block diagram of a software configuration for a mobile device according to an embodiment of the disclosure.

FIG. 7 illustrates a software environment 602 that may be implemented by the DSP 502. The DSP 502 executes operating system drivers 604 that provide a platform from which the rest of the software operates. The operating system drivers 604 provide drivers for the handset hardware with standardized interfaces that are accessible to application software. The operating system drivers 604 include application management services ("AMS") 606 that transfer control between applications running on the handset 400. Also shown in FIG. 7 are a web browser application 608, a media player application 610, and JAVA applets 612. The web browser application 608 configures the handset 400 to operate as a web browser, allowing a user to enter information into forms and select links to retrieve and view web pages. The media player application 610 configures the handset 400 to retrieve and play audio or audiovisual media. The JAVA applets 612 configure the handset 400 to provide games, utilities, and other functionality.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

Also, techniques, systems, subsystems and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein.

What is claimed is:

1. A monitoring system for monitoring a plurality of monitored physical locations, comprising:
    a first storage queue containing rules ready for processing;
    an event storage containing events;
    a plurality of first processor threads configured to execute any one of the rules contained in the first storage queue based on the contents of the event storage; and
    a rules processor configured to receive a plurality of events from a plurality of monitored physical locations, to add the events to the event storage, to remove a first rule from the first storage queue, to provide the first rule to one of the first processor threads for executing, to receive a first result from the one of the first processor threads, and to send a first notification based on the first result;
    wherein at least one of the events comprises information regarding at least one of physical activity and physical inactivity at one or more of the plurality of monitored physical locations.

2. The system of claim 1, wherein the first storage queue contains static rules associated with the monitored physical locations, and further comprising:
    a second storage queue containing dynamic rules associated with the monitored physical locations; and
    a plurality of second processor threads configured to execute any one of the rules contained in the second storage queue based on the contents of the event storage;
    wherein the rules processor is further configured to remove a second rule from the second storage queue, to provide the second rule to one of the second processor threads for executing, to receive a second result from the one of the second processor threads, and to send a second notification based on the second result.

3. The system of claim 2, wherein each of the first processor threads is further configured to return the first rule to the first storage queue if no event in the event storage matches the first rule and if a time associated with the first rule has not expired, and wherein each of the second processor threads is further configured to return the second rule to the second storage queue if no event in the event storage matches the second rule and if a timer associated with the second rule has not expired.

4. The system of claim 2, wherein a dynamic rule is put in the second storage queue when the rules processor receives a trigger sensor event linked with the dynamic rule and wherein a timer associated with the dynamic rule counts time from about when the trigger sensor event is received by the rules processor.

5. The system of claim 1 wherein the first notification is emailed to a monitoring terminal.

6. The system of claim 1 wherein the events indicate at least one of a motion in an elder care location, a door opening in an elder care location, and a window opening in an elder care location.

7. The system of claim 1 wherein the rules contained by the first storage queue are one of a static type rule and a dynamic type rule.

8. The system of claim 1 wherein the rules define a plurality of rule chains, each rule chain associated with one remote environment and including at least one rule, each rule including at least one condition, each condition associated with at least one sensor.

9. The system of claim 8 wherein the condition identifies an expected time range for the at least one associated sensor to generate an event, and wherein the one of the first processor threads generates a negative result when the condition times out and wherein the rules processor sends the first notification indicating an expected event did not occur in the expected time range.

10. A method of monitoring a plurality of locations, comprising:
    adding a plurality of static rules to a static rules queue, each static rule associated with one of the locations;
    adding a plurality of dynamic rules to a dynamic rules queue, each dynamic rule associated with one of the locations;
    adding a plurality of events to an event store, at least some of the events associated with the locations;
    removing a first static rule from the static rules queue for processing;
    returning the first static rule to the static rules queue for later processing;
    matching a first event in the event store with the first static rule, the matching based at least in part on the location associated with the first event and with the first static rule;
    processing the first static rule based on the first event;
    removing a first dynamic rule from the dynamic rules queue for processing;
    returning the first dynamic rule to the dynamic rules queue for later processing;
    matching a second event in the event store with the first dynamic rule, the matching based at least in part on the location associated with the second event and with the first dynamic rule; and
    processing the first dynamic rule based on the second event,
    wherein the static rules are defined with reference to a start time and an end time, and wherein the dynamic rules are defined with reference to an elapsed time since an associated event.

11. The method of claim 10, wherein the static rules and the dynamic rules are associated with one location by an account number.

12. The method of claim 10, wherein at least some of the static rules associated with a location are linked together as a static rule chain, wherein at least some of the dynamic rules associated with the location are linked together as a dynamic rule chain, and further including:
    sending a first positive notification when all the static rules associated with the static rule chain complete successfully, and sending a second positive notification when all the dynamic rules associated with the dynamic rule chain complete successfully.

13. The method of claim 12, further including:
sending a first negative notification when one of the static rules completes unsuccessfully; and
sending a second negative notification when one of the dynamic rules completes unsuccessfully.

14. The method of claim 10 wherein the events associated with the locations indicate that motion has been detected at the locations.

15. A method of providing elder care, comprising:
detecting a plurality of events at an elder care location;
determining if the detection of events occurs during an expected time interval based on a first plurality of rules data; and
sending a first notification that expected events occurred based on the first plurality of rules data.

16. The method of claim 15 further including:
updating the first plurality of rules data with a second plurality of rules data, wherein the updating occurs without recompiling code or restarting virtual machines;
determining if the detection of events occurs during an expected time interval based on the second plurality of rules data; and
sending a second notification that expected events occurred based on the second plurality of rules data.

17. The method of claim 15 wherein the first plurality of rules includes one or more time rules and one or more sensor rules and a chain rule that associates the one or more time rules and the one or more sensor rules with the elder care location.

18. The method of claim 17 wherein the chain rule includes an identification of the chain rule, an identification of the elder care location, an identification of one or more time rules, and a message content of the first notification; wherein the time rules include an identification of the time rule, an identification of the elder care location, an identification of a timing rule content, and a message content of a second notification that expected event did not occur based on the time rule content; and wherein the sensor rules include an identification of the sensor rule, an identification of the elder care location, and an identification of a sensor, an identification of a sensor type.

19. The method of claim 18 wherein the rules are stored as entries in a chain rule table, in a time rule table, and a sensor rule table in a database.

20. The method of claim 15 wherein the rules data includes both static time rules data and dynamic time rules data.

* * * * *